United States Patent
Kim et al.

(10) Patent No.: US 11,045,452 B2
(45) Date of Patent: Jun. 29, 2021

(54) COMPOSITION FOR PREVENTING OR TREATING CANCER COMPRISING A VASCULAR DISRUPTING AGENT AND IMMUNE CHECKPOINT INHIBITOR

(71) Applicant: CHONG KUN DANG PHARMACEUTICAL CORP., Seoul (KR)

(72) Inventors: Soo Jin Kim, Gyeonggi-do (KR); U Ji Kim, Gyeonggi-do (KR); Inhak Choi, Busan (KR); Suna Im, Jeollabuk-do (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 16/633,326

(22) PCT Filed: Jul. 25, 2018

(86) PCT No.: PCT/KR2018/008408
§ 371 (c)(1),
(2) Date: Jan. 23, 2020

(87) PCT Pub. No.: WO2019/022501
PCT Pub. Date: Jan. 31, 2019

(65) Prior Publication Data
US 2020/0163942 A1 May 28, 2020

(30) Foreign Application Priority Data
Jul. 26, 2017 (KR) ........................ 10-2017-0094767

(51) Int. Cl.
*A61K 31/42* (2006.01)
*A61K 31/427* (2006.01)
*A61P 35/02* (2006.01)
*A61K 45/06* (2006.01)

(52) U.S. Cl.
CPC ............ *A61K 31/427* (2013.01); *A61P 35/02* (2018.01); *A61K 45/06* (2013.01)

(58) Field of Classification Search
CPC .................................................. A61K 31/427
See application file for complete search history.

(56) References Cited

U.S. PATENT DOCUMENTS

| | | |
|---|---|---|
| 2011/0021582 A1 | 1/2011 | Choi |
| 2016/0194407 A1 | 7/2016 | Hay |

FOREIGN PATENT DOCUMENTS

| | | |
|---|---|---|
| JP | A 2011-515461 | 5/2011 |
| KR | 10-2009-0102639 A | 9/2009 |
| WO | 2009/119980 A2 | 10/2009 |
| WO | 2016/130839 A1 | 8/2016 |
| WO | 2016/197204 A1 | 12/2016 |
| WO | 2017/059280 A1 | 4/2017 |

OTHER PUBLICATIONS

Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*
International Search Report for PCT/KR2018/008408 dated Nov. 13, 2018. 4 pages.
Martin et al., "The microtubule-depolymerizing agent ansamitocin P3 programs dendritic cells toward enhanced anti-tumor immunity", Cancer Immunol Immunother 2014, 63, published online: Jun. 7, 2014, pp. 925-938.
Lee et al., "Identification of CKD-516: A Potent Tubulin Polymerization Inhibitor with Marked Antitumor Activity against Murine and Human Solid Tumors", Journal of Medicinal chemistry, 2010, vol. 53, No. 17, published on Web Aug. 6, 2010, pp. 6337-6354.
Moon et al., CKD-516 displays vascular disrupting properties and enhances anti-tumor activity in combination with chemotherapy in a murine tumor model, Invest New Drugs, 2014, vol. 32, No. 3, published online: Nov. 8, 2013, pp. 400-411.
Written Opinion of the International Searching Authority for PCT/KR2018/008408 dated Nov. 13, 2018. 5 pages.
Office Action for KR10-2018-0086406 dated Dec. 2, 2019. 10 pages.
Office Action for TW107125942 dated Feb. 23, 2019. 12 pages.
Lavranos et al., "abstract #B92: The tubulin-targeting agent BNC105 potentiates the efficacy of immune checkpoint inhibitors in preclinical models of colorectal cancer," Poster presented at International Conference: Molecular Targets and Cancer Therapeutics, Boston, MA, Nov. 5-9, 2015, Molecular Targets and Cancer Therapeutics, Dec. 2015 14(12)(Supp 2): 1 page.
JP Office Action in Japanese Appln. No. 2020-504027, dated Dec. 15, 2020, 9 pages (with English Translation).
EP Extended European Search Report in European Appln. No. 18838824.3, dated Mar. 19, 2021, 10 pages.
Ferrer et al., "Plinabulin: Tubulin Polymerization Inhibitor Vascular-Disrupting Agent Oncolytic," Drugs of the Future, Jan. 1, 2010, 35(1):11-15.

* cited by examiner

Primary Examiner — Shawquia Jackson
(74) Attorney, Agent, or Firm — Fish & Richardson P.C.

(57) ABSTRACT

The present disclosure provides a composition for preventing or treating cancer comprising (S)—N-(4-(3-(1H-1,2,4-triazole-1-yl)-4-(3,4,5-trimethoxy-benzoyl)phenyl)thiazole-2-yl)-2-amino-3-methylbutanamide or pharmaceutically acceptable salts thereof, and an immune checkpoint inhibitor. The composition of the present disclosure achieves an excellent cancer treatment effect.

15 Claims, 7 Drawing Sheets

[Fig. 1]
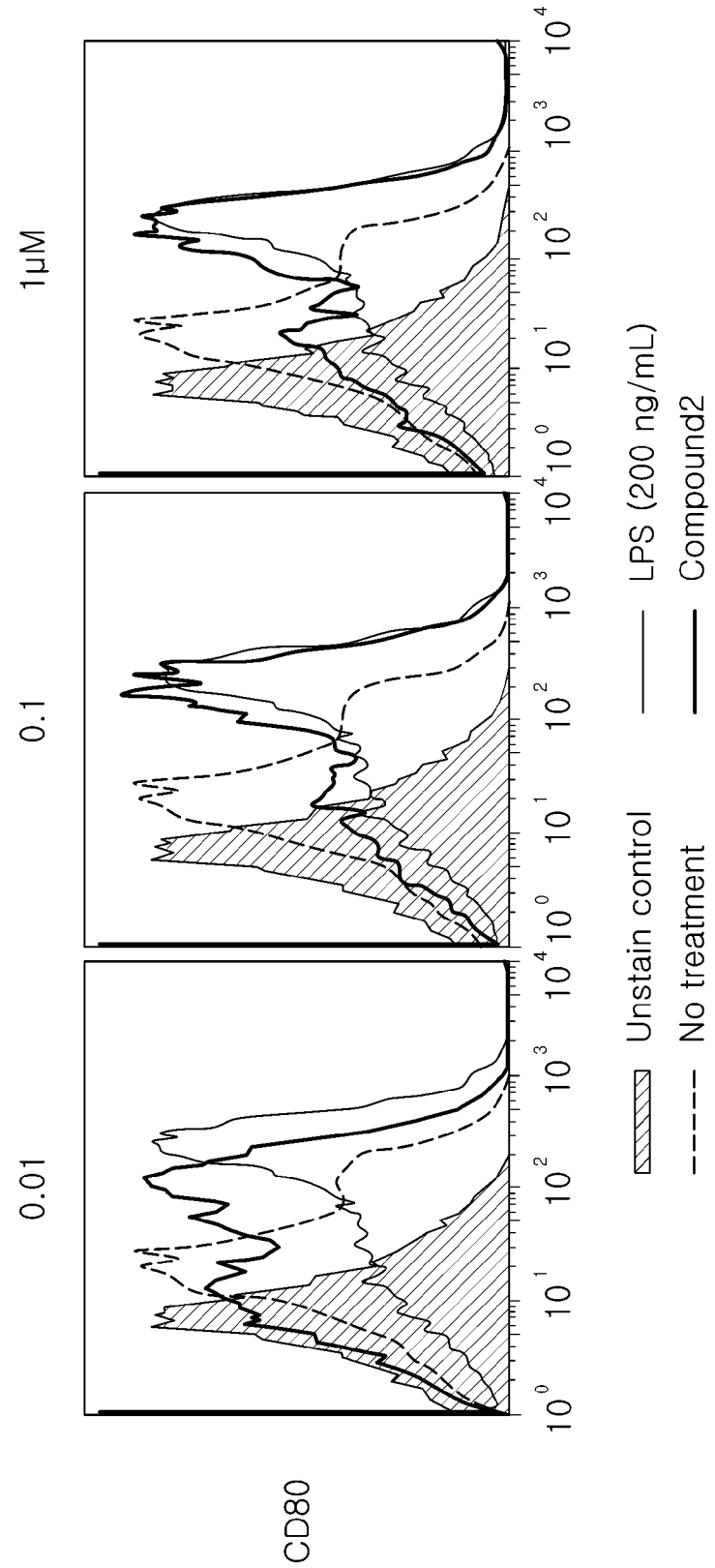

[Fig. 2]
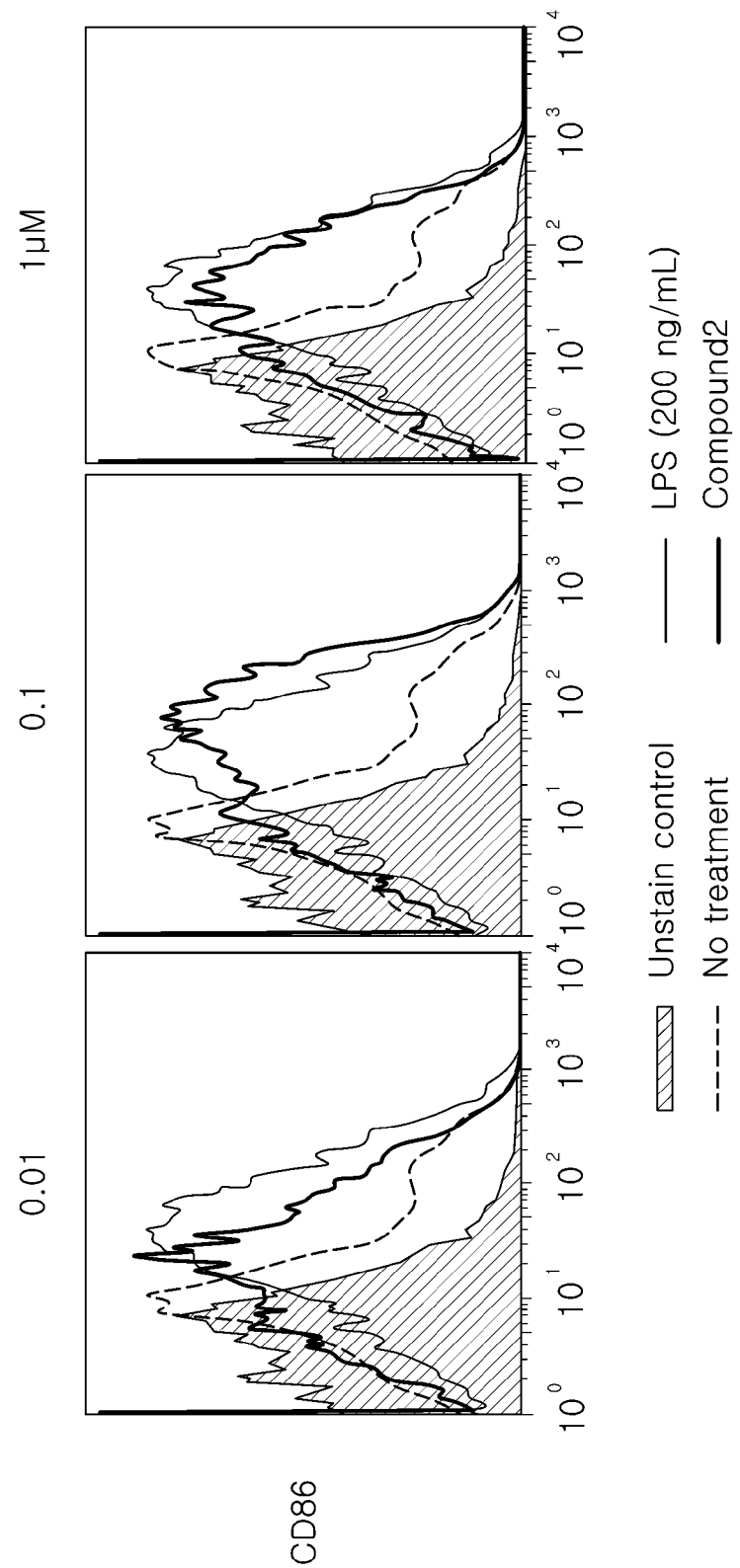

[Fig. 3]
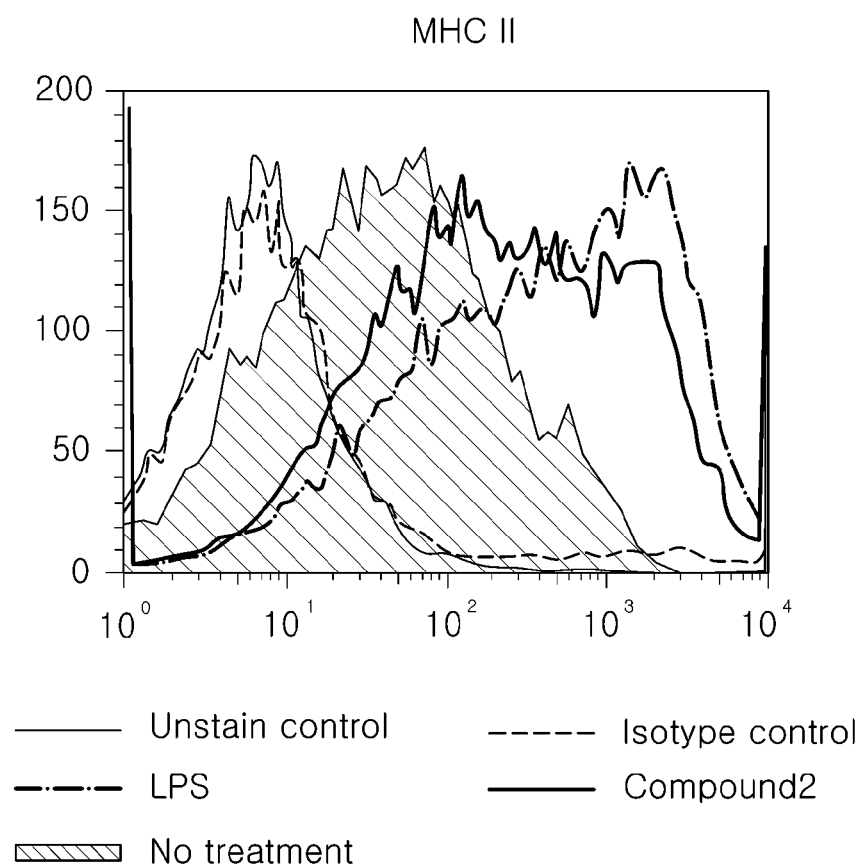

[Fig. 4]
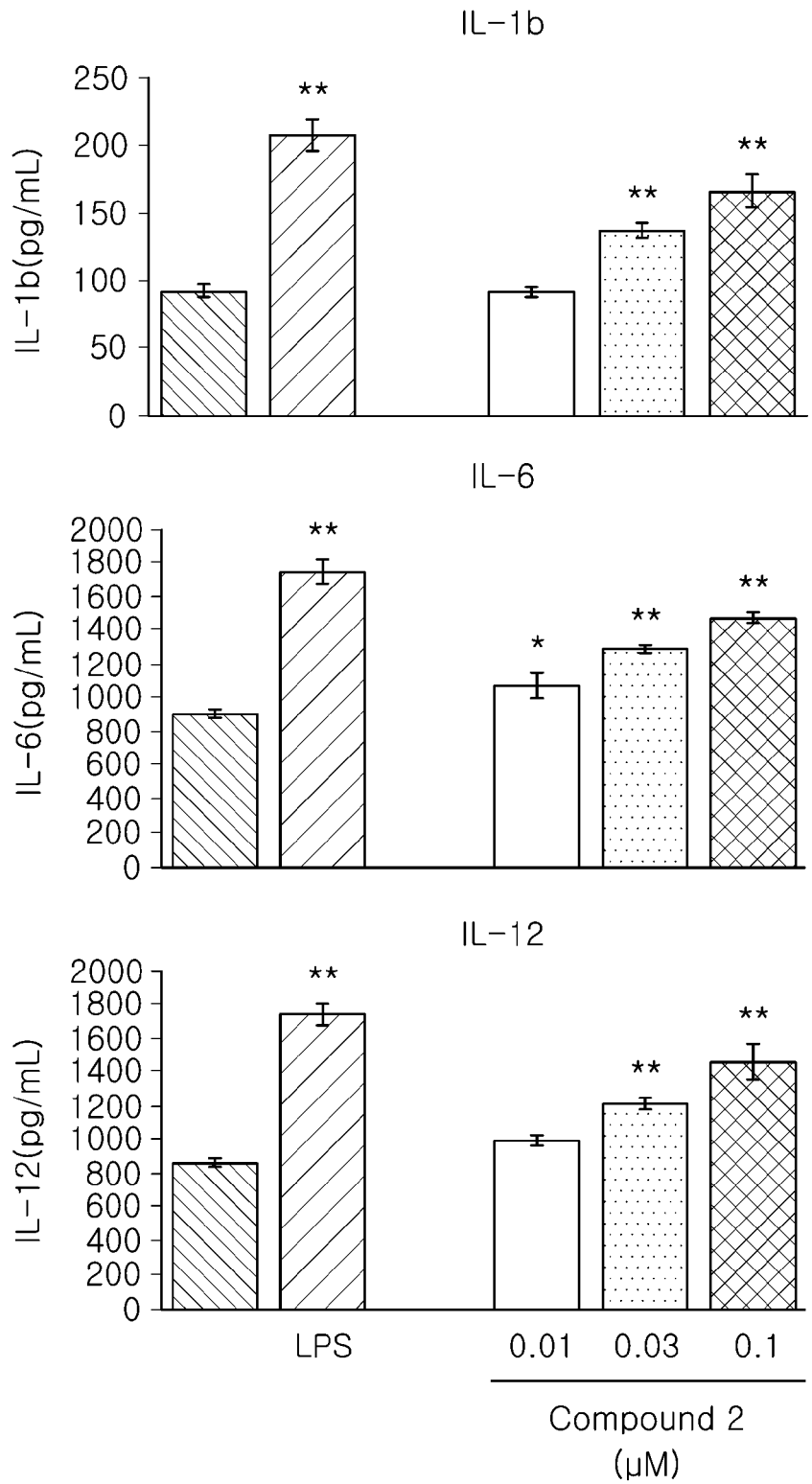

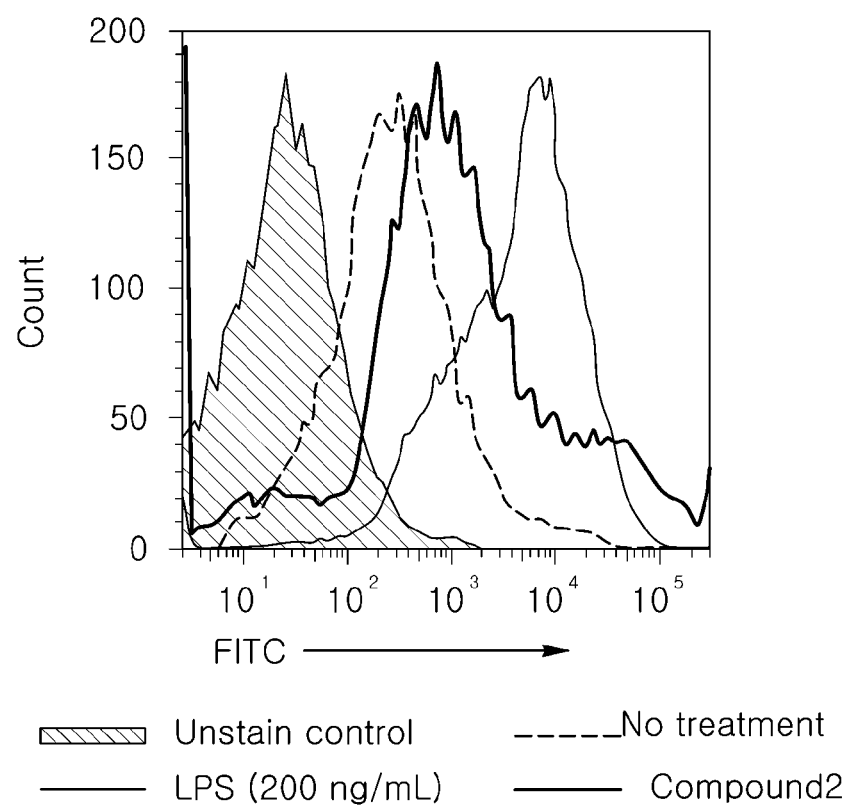
[Fig. 5]

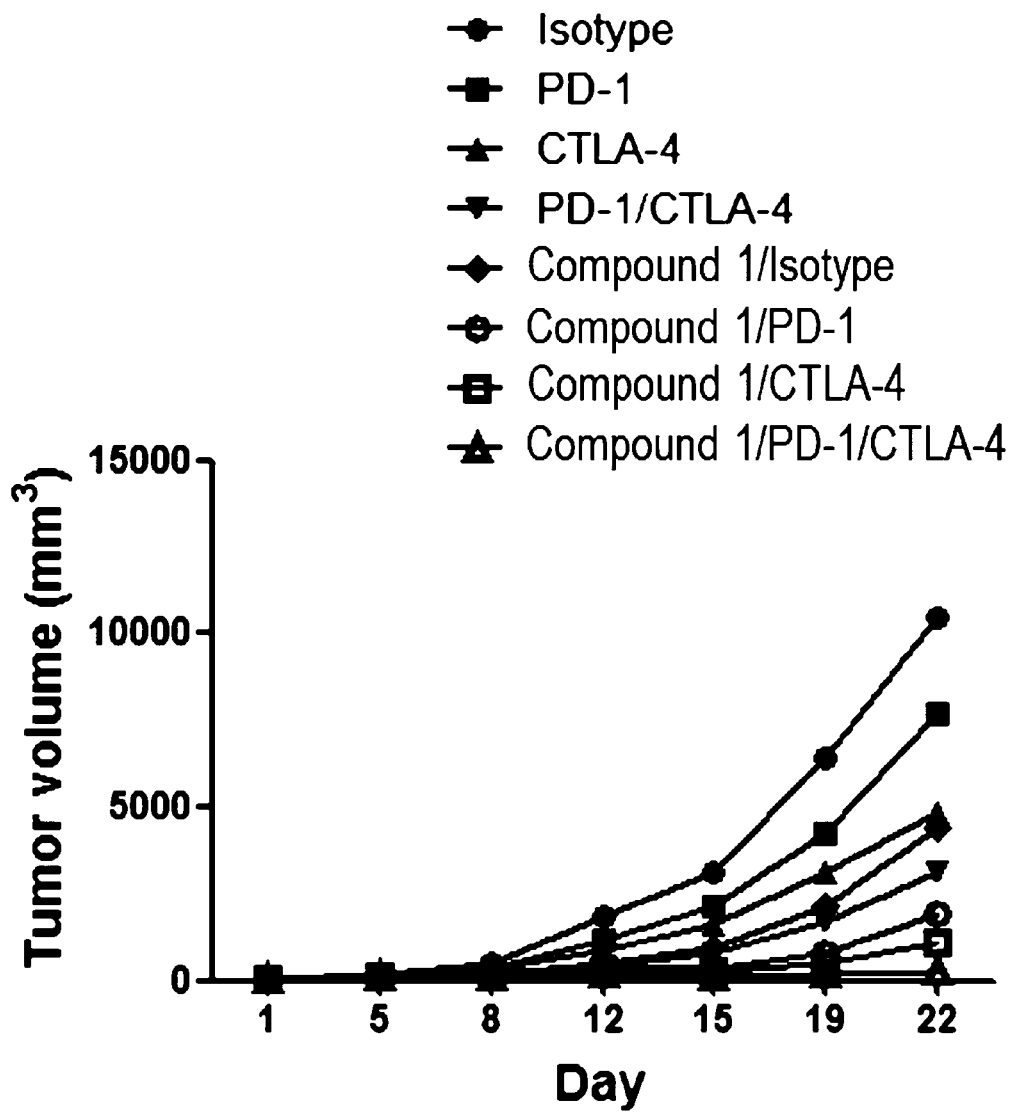
[Fig. 6]

[Fig. 7]
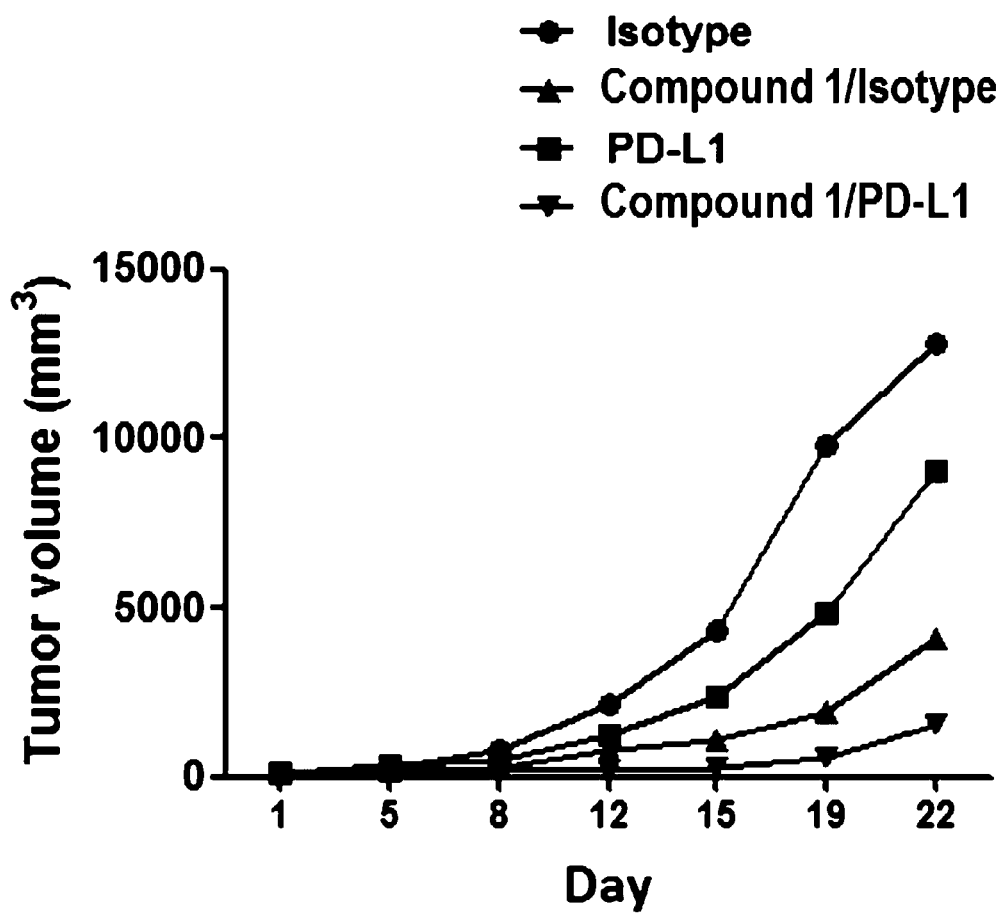

COMPOSITION FOR PREVENTING OR TREATING CANCER COMPRISING A VASCULAR DISRUPTING AGENT AND IMMUNE CHECKPOINT INHIBITOR

TECHNICAL FIELD

The present disclosure relates to a composition for preventing or treating cancer comprising a vascular disrupting agent (VDA) and an immune checkpoint inhibitor.

BACKGROUND ART

As a recent advance in an immunology field results in a more understanding of the immune system of the human body, immunotherapy has been developed as a new tumor therapy, wherein it has an advantage in that patients may use their own immune system, thus gaining an anti-tumor immunity for a long period of time with a less side effect.

A goal of immunotherapy is to produce tumor-specific cytotoxic T lymphocytes (CTL) capable of recognizing tumor cells or tumor antigens, and thus eliminating the tumor cells. In other words, tumor antigen peptides are loaded onto major histocompatibility complexes (MHC), and then are presented to T lymphocytes by means of tumor cells themselves or antigen-presenting cells, thus activating the T lymphocytes and inducing their differentiation into the CTL and an increase in the CTL.

However, most of the tumors in the human body tend to avoid an individual's immune surveillance such that they are difficult to be treated. The causes of such difficulty are as follows: 1) tumor antigens are part of autoantigens, most of which are expressed during a fetal period or expressed in normal cells, or fail to be recognized as an antigen due to a very low degree of inducing immunity, 2) MHC expression by means of tumor cells is poor or tumor antigens are incompletely processed in tumor cells, thus failing to be presented at all, 3) most of the tumor cells may not express costimulatory molecules essential for antigen presentation, and 4) such tumor cells may avoid immune surveillance by means of inhibitory cytokines secreted by tumors.

Meanwhile, a vascular disrupting agent (VDA) sets a goal at selectively destroying the cytoskeletal microtubules of vascular endothelial cells and thus quickly and selectively disrupting tumor blood vessels formed there, wherein the VDA may also induce ischemic necrosis of cells located at the center of tumors. However, if treated alone, most of the VDAs have a problem in that tumors may promptly regrow from viable rims, thus reducing the therapeutic usefulness of such medicaments.

PRIOR ART REFERENCES

Patent Documents

WO2009/119980
WO2016/130839
WO2016/197204

Non-Patent Document

Cancer immunology immunotherapy 2014; 63:925-938

DISCLOSURE OF INVENTION

Technical Problem

The present inventors have attempted various studies to provide a novel composition for preventing or treating cancer and a treatment method thereof, which may make the most of advantages of immunotherapeutic agents using the immunotherapy, while solving problems with a single use of the VDA.

Solution to Problem

An objective of the present disclosure is to provide a composition for preventing or treating cancer comprising a vascular disrupting agent (VDA) and an immune checkpoint inhibitor.

An objective of the present disclosure is to provide a method for treating cancer comprising an administration of the VDA and the immune checkpoint inhibitor into an individual in need.

An objective of the present disclosure is to provide a use of the VDA and the immune checkpoint inhibitor for preparing a medicament for cancer treatment.

An objective of the present disclosure is to provide a composition comprising the VDA and the immune checkpoint inhibitor for use in treating cancer.

Advantageous Effects of Invention

A composition of the present disclosure achieves an excellent activity of preventing or treating cancer, and has an advantage in having a lower possibility of tumor recurrence. Therefore, the composition of the present disclosure may be applied for preventing, reducing or treating cancer.

BRIEF DESCRIPTION OF DRAWINGS

FIG. 1 shows an increase in expression of CD80, a mature dendritic cell marker, according to treatment with a compound of a Formula 2.

FIG. 2 shows an increase in expression of CD86, a mature dendritic cell marker, according to treatment with the compound of the Formula 2.

FIG. 3 shows an increase in expression of MHC II, a mature dendritic cell marker, according to treatment with the compound of Formula 2.

FIG. 4 shows an increase in a secretion amount of IL-lb, IL-6 and IL-12, according to treatment with the compound of the Formula 2.

FIG. 5 shows an increase in phagocytosis of dendritic cells, according to treatment with the compound of the Formula 2.

FIG. 6 shows a cancer treatment effect according to a single or combined administration of a vascular disrupting agent and an immune checkpoint inhibitor (PD-1, CTLA-4 or both of them) in a cancer animal model.

FIG. 7 shows a cancer treatment effect according to a single or combined administration of the VDA and the immune checkpoint inhibitor (PD-L1) in a cancer animal model.

BEST MODE FOR CARRYING OUT THE INVENTION

As a result of making efforts to achieve the objectives above, the present inventors have completed a pharmaceutical composition for preventing or treating cancer comprising a vascular disrupting agent (VDA) and an immune checkpoint inhibitor.

The VDA sets a goal at selectively destroying the cytoskeletal microtubules of vascular endothelial cells and thus quickly and selectively disrupting tumor blood vessels formed there. Also, the VDA may induce ischemic necrosis of cells located at the center of tumors.

In the present disclosure, a compound used as said VDA is (S)—N-(4-(3-(1H-1,2,4-triazole-1-yl)-4-(3,4,5-trimethoxybenzoyl)phenyl)thiazole-2-yl)-2-amino-3-methylbutanamide represented by a following Formula 1 or pharmaceutically acceptable salts thereof.

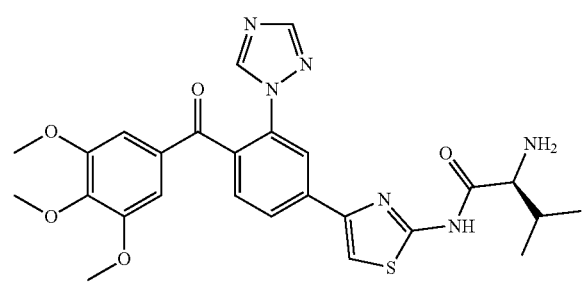

[Formula 1]

In the present disclosure, the compound of the Formula 1 above may be prepared, for example, by means of a preparation method disclosed in International Patent Publication WO 2009-119980, but is not limited thereto.

In the present disclosure, pharmaceutically acceptable salts mean the salts conventionally used in a pharmaceutical industry, wherein they are, for example, inorganic ion salts prepared from calcium, potassium, sodium, magnesium or the like; inorganic acid salts prepared from hydrochloric acid, nitric acid, phosphoric acid, bromic acid, iodic acid, perchloric acid, sulfuric acid or the like; organic acid salts prepared from acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid or the like; sulfonic acid salts prepared from methanesulfonic acid, ethanesulfonic acid, benzenesulfonic acid, p-toluenesulfonic acid, naphthalenesulfonic acid or the like; amino acid salts prepared from glycine, arginine, lysine, etc.; amine salts prepared from trimethylamine, triethylamine, ammonia, pyridine, picoline, etc.; or the like, but types of the salts meant in the present disclosure are not limited by the above-listed salts.

Particularly, the salt of (S)—N-(4-(3-(1H-1,2,4-triazole-1-yl)-4-(3,4,5-trimethoxybenzoyl)phenyl)thiazole-2-yl)-2-amino-3-methylbutanamide may be hydrochloride.

In the present disclosure, an active metabolite of the compound of the Formula 1 above may be (4-(2-aminothiazole-4-yl)-2-(1H-1,2,4-triazole-1-yl)phenyl)(3,4,5-trimethoxyphenyl)methanone represented by a following Formula 2. The term "active metabolite" above is a substance actually showing pharmacological activity in a treatment object, among substances produced during a metabolic process of assimilation or catabolism in a body.

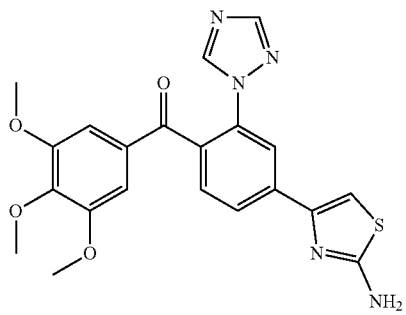

[Formula 2]

In the present disclosure, said pharmaceutical composition comprising the compound of the Formula 1 for preventing or treating cancer is present as a compound of the Formula 2 above according to a metabolic process in an individual, thus achieving an effect of preventing, reducing or treating cancer.

The compound of the Formula 1 according to the present disclosure quickly and selectively disrupts tumor blood vessels, so as not only to cause ischemic necrosis of cells located at the center of tumors, but also to activate dendritic cells.

According to one embodiment of the present disclosure, the compound of the Formula 2 above promotes maturation of dendritic cells (DC), increases phagocytosis, and increases foreign antigen-presenting capacity (FIGS. 1 to 5).

The dendritic cells are those capable of inducing anti-tumor immunity, wherein they obtain antigens through phagocytosis, etc., and express the antigens by loading antigen peptides onto the MHC, so as to strongly induce the activity of T lymphocytes having an antigen-specific T cell receptor. Also, when activated, the dendritic cells express IL12 to prevent apoptosis of T lymphocytes, induce differentiation of T lymphocytes and activity of the CTL, and increase activity of natural killer cells, such that such cells achieve characteristics of increasing anti-tumor immunity.

Thus, in the inventive pharmaceutical composition for preventing or treating cancer, the compound of the Formula 1 and the compound of the Formula 2, which is an active metabolite thereof, achieve not only an effect of serving as a vascular disrupting agent, but also action effects of activating the dendritic cells and increasing the phagocytosis and the foreign antigen-presenting capacity.

In the present disclosure, an immune checkpoint inhibitor inhibits cancer from evading immunity by disrupting an immune checkpoint, which prevents a progress of immune responses in cancer with a high immunosuppressive capacity, such that it may treat cancer.

The immune checkpoint inhibitor is a novel tumor therapeutic agent developed as a result of acquiring a more understanding of the immune system of the human body due to an advance in an immunology field, wherein such inhibitor has been widely used in an anti-cancer strategy. As an exemplary mechanism for using the inhibitor and thus achieving an anti-cancer effect, there are a T lymphocyte inhibitory mechanism by means of CTLA-4 and a PD-1/PD-L1 mechanism for inhibiting T lymphocytes, which are already activated. However, it is reported that the treatment with immune checkpoint inhibitor alone has limits such as a low therapeutic efficiency, an insignificant effect and the like.

However, the inventive composition for preventing or treating cancer helps prevent and treat cancer through an immunotherapy due to a synergistic and complementary effect, in such a way that the compound of the Formula 1 (the VDA) and the immune checkpoint inhibitor, which are anti-cancer medicaments with a different therapeutic mechanism, are administered in combination with each other.

The immune checkpoint inhibitor may be an antibody, a fusion protein, an aptamer or an immune checkpoint protein-binding fragment thereof. For example, the immune checkpoint inhibitor is an anti-immune checkpoint protein antibody or an antigen-binding fragment thereof.

In a certain example, the immune checkpoint inhibitor is selected from an antiCTLA4 antibody, a derivative thereof or an antigen-binding fragment thereof; an antiPD-L1 antibody, a derivative thereof or an antigen-binding fragment thereof; an antiLAG-3 antibody, a derivative thereof or an antigen-binding fragment thereof; an antiOX40 antibody, a derivative thereof or an antigen-binding fragment thereof; an antiTIM3 antibody, a derivative thereof or an antigen-binding fragment thereof; and an anti-PD-1 antibody, a derivative thereof or an antigen-binding fragment thereof.

For example, the immune checkpoint inhibitor may be selected from ipilimumab, a derivative thereof or an antigen-binding fragment thereof; tremelimumab, a derivative thereof or an antigen-binding fragment thereof; nivolumab, a derivative thereof or an antigen-binding fragment thereof; pembrolizumab, a derivative thereof or an antigen-binding fragment thereof; pidilizumab, a derivative thereof or an antigen-binding fragment thereof; atezolizumab, a derivative thereof or an antigen-binding fragment thereof; durvalumab, a derivative thereof or an antigen-binding fragment thereof; avelumab, a derivative thereof or an antigen-binding fragment thereof; BMS-936559, a derivative thereof or an antigen-binding fragment thereof; BMS-986016, a derivative thereof or an antigen-binding fragment thereof; GSK3174998, a derivative thereof or an antigen-binding fragment thereof; TSR-022, a derivative thereof or an antigen-binding fragment thereof; MBG453, a derivative thereof or an antigen-binding fragment thereof; LY3321367, a derivative thereof or an antigen-binding fragment thereof; and IMP321 recombinant fusion protein. Any immune checkpoint inhibitor may be used without limitation, as long as it is an antibody or other forms thereof usable as the immune checkpoint inhibitor.

Particularly, it is preferably at least one selected from the group consist of an antiCTLA4 antibody, an anti-PD-1 antibody, an anti-LAG-3 antibody, an anti-OX40 antibody, an anti-TIM3 antibody and an anti-PD-L1 antibody. The antibody may be used, for example, in such a way that it is purchased from a conventional antibody manufacturer, etc., or prepared according to a known method for preparing antibodies.

The immune checkpoint inhibitor may be a small molecule compound that has an effect as immune checkpoint inhibitor described above or is involved in its inhibitory mechanism. For example, these small molecule compounds may be small molecule compound that bind to immune checkpoint protein or is involved in the mechanism related with inhibiting of immune checkpoint.

Particularly, the small molecule compounds may be BMS-202 (Resource: BMS), BMS-8 (Resource: BMS), CA170 (Resource: Curis/Aurigene), CA327 (Resource: Curis/Aurigene), Epacadostat, GDC-0919, BMS-986205 and the like.

Any immune checkpoint inhibitor may be used without limitation, as long as it is a small molecule compounds usable as the immune checkpoint inhibitor or having a related effect.

The composition of the present disclosure is administered in combination with the compound of the Formula 1 (the VDA) and the immune checkpoint inhibitor, thus achieving a remarkable activity of preventing and treating cancer due to a synergistic and complementary effect according to such combined use.

As one example of a therapeutic mechanism, the composition of the present disclosure may have a remarkable effect on preventing and treating cancer as follows, but is not limited thereto. The compound of the Formula 1 activates dendritic cells, and thus the activation of T lymphocytes may sequentially occur. In a phase in which the T lymphocytes are activated, or in a phase in which the activated T lymphocytes recognize cancer cells to kill them, the immune checkpoint may disrupt the phases, so as to inhibit the activation of T lymphocytes. However, the immune checkpoint inhibitor, which is administered in combination with the compound of the Formula 1, may disrupt the phase of inhibiting the activation of T lymphocytes, so as to maintain the activity of T lymphocytes. Thus, it is possible to achieve a synergy effect on the activity of preventing or treating cancer, by means of a combination of different mechanisms: the one is that T lymphocytes are activated by the compound of the Formula 1, and the other is that the inhibition of T lymphocytes from activation by cancer cells is disrupted by the immune checkpoint inhibitor.

In one embodiment of the present disclosure, it was identified that a combined administration of the compound of the Formula 1, and the anti-PD-1 antibody, the anti-CTLA-4 antibody or both of them achieved an increased cancer treatment effect in comparison with a single administration (FIG. 6).

In one embodiment of the present disclosure, it was identified that a combined administration of the compound of the Formula 1 and the anti-PD-L1 antibody achieved an increased cancer treatment effect in comparison with a single administration (FIG. 7).

Therefore, the composition comprises the compound of the Formula 1 and at least one selected from the group consist of the anti-CTLA4 antibody, the anti-PD-1 antibody and the anti-PD-L1 antibody. Particularly, the composition comprises the compound of the Formula 1 and the anti-CTLA4 antibody. Particularly, the composition comprises the compound of the Formula 1 and the anti-PD-1 antibody. Particularly, the composition comprises the compound of the Formula 1 and the anti-PDL1 antibody. Particularly, the composition comprises the compound of the Formula 1, the anti-CTLA4 antibody and the anti-PD-1 antibody.

In the present disclosure, the composition of the present disclosure may be valuably used for preventing or treating cancer. The cancer may be various kinds of cancer in the human body, gynecological tumor, endocrine system cancer, central nervous system tumor, ureteral cancer, etc., particularly including lung cancer, gastric cancer, liver cancer, bone cancer, pancreatic cancer, skin cancer, head and neck cancer, skin melanoma, uterine cancer, ovarian cancer, colorectal cancer, breast cancer, sarcoma of uterus, fallopian tube carcinoma, internal endometrium carcinoma, cervical carcinoma, vaginal carcinoma, vulvar carcinoma, esophagus cancer, laryngeal cancer, small bowel neoplasm, thyroid cancer, parathyroid cancer, soft tissue sarcoma, urethral cancer, penis cancer, prostate cancer, multiple myeloma, chronic or acute leukemia, solid tumor of childhood, lymphoma (such as, differentiated lymphoma, first central nervous system lymphoma), bladder cancer, renal cancer, renal cell carcinoma, renal pelvic carcinoma, spinal axis tumor, brainstem glioma, merkel cell carcinoma, urinary tract neoplasm or pituitary gland adenoma, but is not limited thereto. More particularly, the pharmaceutical composition of the present disclosure may be used in for preventing or treating cancer selected from the group consist of colorectal cancer, skin melanoma, lung cancer, gastric cancer, lymphoma, merkel cell carcinoma, urinary tract neoplasm and multiple myeloma.

The pharmaceutical composition of the present disclosure may be formulated into a preparation by using a pharmaceutically acceptable carrier according to a method, which may be easily performed by those skilled in the art, to which the present disclosure pertains, such that such composition can be prepared in a mono-dose form or prepared by being inserted into a multi-dose container.

The pharmaceutically acceptable carrier is the one conventionally used in formulating a preparation, wherein such carrier includes, but not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propylhydroxybenzoate, talc, magnesium stearate, mineral oil and the like. Besides the components, the pharmaceutical composition of the present disclosure may further comprise lubricant, humectant, sweetening agent, flavoring agent, emulsifier, suspending agent, preservative, etc. Suitable pharmaceutically acceptable carriers and preparations are described in detail in Remington's Pharmaceutical Sciences (19th ed., 1995).

The composition of the present disclosure may comprise two types of separate preparations and may be also composed of one preparation.

The composition of the present disclosure may be orally or parenterally administered (for example, applied intravenously, subcutaneously, intraperitoneally or locally) according to a targeted method.

In the present disclosure, (S)—N-(4-(3-(1H-1,2,4-triazole-1-yl)-4-(3,4,5-trimethoxybenzoyl)phenyl)thiazole-2-yl)-2-amino-3-methylbutanamide or pharmaceutically acceptable salts thereof may be orally or parenterally administered, and preferably orally administered.

Also, the immune checkpoint inhibitor may be orally or parenterally administered.

For example, the antibody, the fusion protein, the aptamer or the immune checkpoint protein-binding fragment thereof as the immune checkpoint inhibitor may be parenterally administered.

For example, the small molecule compounds as the immune checkpoint inhibitor may be orally or parenterally administered.

In the composition of the present disclosure, the suitable range of doses of the effective components above varies depending on a patient's weight, age, gender, health condition, diet, administration time, administration method, excretion rate, disease severity and the like. A daily dose of (S)—N-(4-(3-(1H-1,2,4-triazole-1-yl)-4-(3,4,5-trimethoxybenzoyl)phenyl)thiazole-2-yl)-2-amino-3-methylbutanamide or pharmaceutically acceptable salts thereof is about 1 to 20 mg/m$^2$, preferably 5 to 15 mg/m$^2$. Also, a daily dose of the antibody, the fusion protein, the aptamer or the immune checkpoint protein-binding fragment thereof as the immune checkpoint inhibitor of the present disclosure is about 0.1 to 50 mg/kg, preferably 1 to 30 mg/kg. A daily dose of the small molecule compounds as the immune checkpoint inhibitor of the present disclosure is about 1 to 1500 mg, preferably 200 to 800 mg.

Moreover, in the composition of the present disclosure, a suitable interval of administering the effective components above may depend on said dose. (S)—N-(4-(3-(1H-1,2,4-triazole-1-yl)-4-(3,4,5-trimethoxybenzoyl)phenyl)thiazole-2-yl)-2-amino-3-methylbutanamide or pharmaceutically acceptable salts thereof may be administered once a day or once every three weeks, particularly twice a week, but is not limited thereto. In addition, the immune checkpoint inhibitor of the present disclosure may be administered once a day or once every three weeks, but is not limited thereto.

The present disclosure provides a method for treating cancer comprising an administration of the inventive VDA and the immune checkpoint inhibitor into an individual in need. In the present disclosure, the term "individual" comprises mammals, particularly humans. The treatment method comprises an administration of a therapeutically effective amount, wherein the term "therapeutically effective amount" refers to an amount of the inventive VDA and the immune checkpoint inhibitor, which is effective for cancer treatment. The VDA and the immune checkpoint inhibitor above may be administered sequentially in any order or simultaneously.

The present disclosure is to provide a use of the VDA and the immune checkpoint inhibitor for preparing a medicament for cancer treatment. The composition comprising the inventive VDA and the immune checkpoint inhibitor for preparing a medicament may be mixed with an acceptable carrier, etc., and may further comprise other agents.

The present disclosure is to provide the composition comprising the VDA and the immune checkpoint inhibitor for use in treating cancer.

Matters mentioned in the use, composition, treatment method of the present disclosure are equally applied unless they contradict each other.

MODE FOR THE INVENTION

Hereinafter, the configurations and effects of the present disclosure will be described in more detail through Examples. However, the following Examples are provided only for the purpose of illustrating the present disclosure, and thus the scope of the present disclosure is not limited thereto.

<Example 1> Effect of Compound of Formula 2 on Increasing Activity of Dendritic Cells 1. Experimental Method
Preparation of Mouse Bone Marrow-Derived Dendritic Cells (BM-DC)
Mouse bone marrow-derived dendritic cells (BM-DC) were obtained from a femur of BALB/c or C57BL/6 mouse. The cells were kept with Dulbecco's modified Eagle medium (DMEM) containing 40 ng/mL of rmGM-CSF (JW Creagene, Sungnam, Korea) and 20 ng/mL of rmIL-4 (JW CreaGene), and containing 10% heat-inactivated FBS (Hyclone), 100 U/ml of penicillin, 100 μg/ml of streptomycin (Hyclone) and 50 μM of 2-mercaptoethanol (Sigma-Aldrich, Inc., St. Louis, Mo., USA).

Preparation of Active Compound
A compound of a Formula 2 (Compound 2), which was an active metabolite of the compound of the Formula 1, was dissolved in DMSO, and diluted with a medium of the mouse bone marrow-derived dendritic cells so as to prepare active compound.

Identification of Phenotype of Dendritic Cells
To identify a phenotype of dendritic cells, the mouse bone marrow-derived dendritic cells were treated with the compound of the Formula 2 for 24 hours, and then were dyed with an antibody (antibody to anti-mouse CD80, anti-mouse CD86 or anti-mouse MHC II) to a cell surface marker of the mouse bone marrow-derived dendritic cells as well as an isotype control antibody. Flow cytometry was performed by using FACS Canto II flow cytometer (Becton Dickinson).

Measurement of Cytokines Produced by Dendritic Cells

To identify a change in secretion of cytokines, the mouse bone marrow-derived dendritic cells were treated with the compound of the Formula 2 for 24 hours, and then the cytokines were measured by using a cell culture medium. An immunoassay kit (R&D system) was used for measuring cytokines, and thus IL-1β, IL-6 and IL-12 were measured.

Measurement of Phagocytosis of Dendritic Cells

To identify phagocytosis of dendritic cells, the mouse bone marrow-derived dendritic cells ($2 \times 10^6$/well) were treated with 100 nM of the compound of the Formula 2 for 18 hours, and then added with OVA-microsphere containing ovalbumin tagged with fluorescein isothiocyanate (FITC), so as to be cultured for 2 hours. Completely cultured cells were washed with PBS, and then the cells were collected, fixed with paraformaldehyde, and analyzed with a flow cytometer.

Statistical Analysis

A statistical significance between a control group and a treated group was verified by using student t-test.

2. Experimental Results

Maturation of Dendritic Cells

Results of treating mouse bone marrow-derived dendritic cells with the compound of the Formula 2 were shown in FIGS. 1 to 3. FIGS. 1, 2 and 3 show results of identifying a phenotype with CD80, CD86 and MHC II as a cell marker, respectively. As seen in FIGS. 1 and 2 above, it was identified that CD80 and CD86 were increased in all the groups administered at concentration of 0.01, 0.1 and 1 μM. FIG. 3 shows results at a concentration of 100 nM, wherein it was identified that MHC II was increased as a phenotype of mature dendritic cells. From the results above, it was identified that the compound of the Formula 2 matured dendritic cells.

Increase in Production of Cytokines

Results of cytokines changed according to treatment with the compound of the Formula 2 were shown in FIG. 4. As a result of treating the mouse bone marrow-derived dendritic cells with the compound of the Formula 2, it was identified that IL-1*?*, IL-6 and IL-12 were increased in all the groups administered with the compound of the Formula 2. From the results above, it was identified that the compound of the Formula 2 matured dendritic cells.

Increase in Phagocytosis of Dendritic Cells

Results of measuring the phagocytosis of dendritic cells were shown in FIG. 5. As a result of analyzing a fluorescence intensity by using a flow cytometer, it was identified that the compound of the Formula 2 increased the phagocytosis of dendritic cells, and thus it was identified that the phagocytosis of dendritic cells was increased with regard to foreign antigens.

<Example 2> Synergic Effect in Cancer Treatment by Compound of Formula 1 and Immune Checkpoint Inhibitor (1)

1. Experimental Method

MC38 ($8 \times 10^4$ cell), a mouse colorectal cancer cell line, was subcutaneously transplanted to a C57BL/6 mouse. When a size of cancer reaches 40-60 mm³, a vehicle or 5 mg/kg of the compound of the Formula 1 was intraperito-neally injected into the mouse twice a week. Also, 1 ug/uL (200 ug/200 uL/mouse) of an anti-PD-1 antibody, an anti-CTLA-4 antibody or both thereof (purchased from BioX-Cell) was intraperitoneally injected into the mouse twice a week, in one day after administering a vehicle or the compound of the Formula 1. A size of cancer and a weight were measured twice a week.

2. Experimental Results

Experimental results above were shown in FIG. 6.

In the cancer animal model above, the compound of the Formula 1 and the anti-PD-1 antibody and the anti-CTLA-4 antibody remarkably inhibited a growth of cancer. Particularly, the compound of the Formula 1 achieved a very high therapeutic potential with a synergy effect, when administered in combination with the anti-PD-1 antibody or the anti-CTLA-4 antibody, respectively. Furthermore, an anti-cancer effect was most increased in an experimental group, in which the compound of the Formula 1 was administered in a third combination with the anti-PD-1 antibody and the anti-CTLA-4 antibody, and thus it was identified that cancer was completely eradicated in two of ten experimental animals. From the results above, it was identified that a combined administration of the compound of the Formula 1 and the immune checkpoint inhibitor achieved a remarkably excellent anti-cancer effect, while having a synergy effect on cancer treatment.

<Example 3> Synergic Effect in Cancer Treatment by Compound of Formula 1 and Immune Checkpoint Inhibitor (2)

1. Experimental Method

MC38 ($8 \times 10^4$ cell), a mouse colorectal cancer cell line, was subcutaneously transplanted to a C57BL/6 mouse. When a size of cancer reaches 40-60 mm³, a vehicle or 5 mg/kg of the compound of the Formula 1 was intraperito-neally injected into the mouse twice a week. Also, 1 ug/uL (200 ug/200 uL/mouse) of an anti-PD-L1 antibody was intraperitoneally injected into the mouse twice a week, in one day after administering a vehicle or the compound of the Formula 1. A size of cancer and a weight were measured twice a week.

2. Experimental Results

The experimental results above were shown in FIG. 7.

In the cancer animal model above, the compound of the Formula 1 and the antiPD-L1 antibody remarkably inhibited a growth of cancer. Particularly, the compound of the Formula 1 achieved a very high therapeutic potential with a synergy effect, when administered in combination with the anti-PD-L1 antibody. From the results above, it was identified that a combined administration of the compound of the Formula 1 and the immune checkpoint inhibitor achieved a remarkably excellent anti-cancer effect, while having a synergy effect on cancer treatment.

The invention claimed is:

1. A pharmaceutical composition for treating cancer comprising (S)—N-(4-(3-(1H-1,2,4-triazole-1-yl)-4-(3,4,5-trimethoxybenzoyl)phenyl)thiazole-2-yl)-2-amino-3-methylbutanamide represented by a following Formula 1 or a pharmaceutically acceptable salt thereof, and an immune checkpoint inhibitor at least one selected from an anti-CTLA4 antibody or an antigen binding fragment thereof; an anti-PD-L1 antibody or an antigen binding fragment thereof; and an anti-PD-1 antibody or an antigen binding fragment thereof,

[Formula 1]

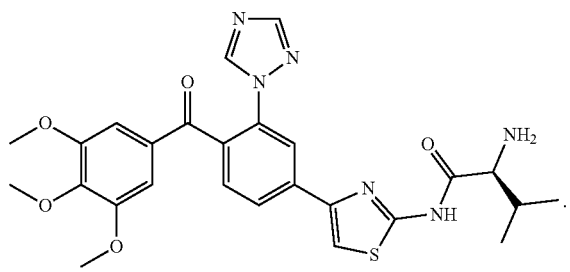

2. The pharmaceutical composition according to claim 1, wherein the pharmaceutically acceptable salt of (S)—N-(4-(3-(1H-1,2,4-triazole-1-yl)-4-(3,4,5-trimethoxybenzoyl)phenyl)thiazole-2-yl)-2-amino-3-methylbutanamide is hydrochloride.

3. The pharmaceutical composition according to claim 1, wherein an active metabolite of the compound represented by the Formula 1 above is (4-(2-aminothiazole-4-yl)-2-(1H-1,2,4-triazole-1-yl)phenyl)(3,4,5-trimethoxyphenyl)methanone represented by a following Formula 2

[Formula 2]

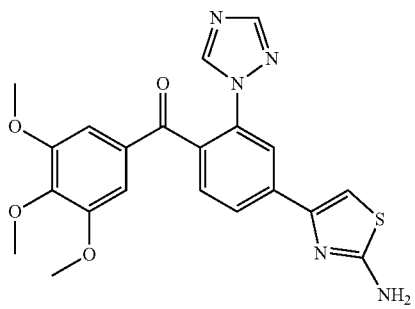

4. The pharmaceutical composition according to claim 1, wherein the immune checkpoint inhibitor is the anti-PD-1 antibody, the anti-CTLA-4 antibody or both thereof.

5. The pharmaceutical composition according to claim 1, wherein the immune checkpoint inhibitor is the anti-PD-1 antibody and the anti-CTLA-4 antibody.

6. The pharmaceutical composition according to claim 1, wherein the cancer is one selected from the group consist of colorectal cancer, skin melanoma, lung cancer, gastric cancer, prostate cancer, lymphoma, merkel cell carcinoma, urinary tract neoplasm and multiple myeloma.

7. A method for treating cancer comprising an administration of (S)—N-(4-(3-(1H-1,2,4-triazole-1-yl)-4-(3,4,5-trimethoxybenzoyl)phenyl)thiazole-2-yl)-2-amino-3-methylbutanamide represented by a following Formula 1 or a pharmaceutically acceptable salt thereof, and an immune checkpoint inhibitor at least one selected from an anti-CTLA4 antibody or an antigen binding fragment thereof; an anti-PD-L1 antibody or an antigen binding fragment thereof; and an anti-PD-1 antibody or an antigen binding fragment thereof into an individual in need

[Formula 1]

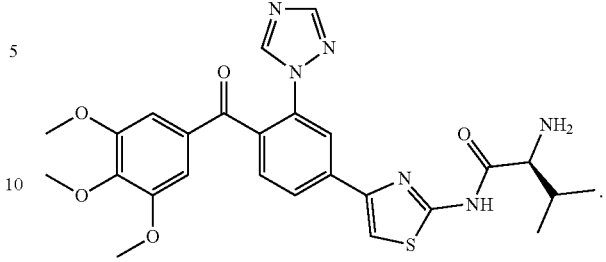

8. The method according to claim 7, wherein the pharmaceutically acceptable salt of (S)—N-(4-(3-(1H-1,2,4-triazole-1-yl)-4-(3,4,5-trimethoxybenzoyl)phenyl)thiazole-2-yl)-2-amino-3-methylbutanamide is hydrochloride.

9. A composition comprising (S)—N-(4-(3-(1H-1,2,4-triazole-1-yl)-4-(3,4,5-trimethoxybenzoyl)phenyl)thiazole-2-yl)-2-amino-3-methylbutanamide represented by a following Formula 1 or a pharmaceutically acceptable salt thereof, and an immune checkpoint inhibitor at least one selected from an anti-CTLA4 antibody or an antigen binding fragment thereof; an anti-PD-L1 antibody or an antigen binding fragment thereof; and an anti-PD-1 antibody or an antigen binding fragment thereof for use in treating cancer

[Formula 1]

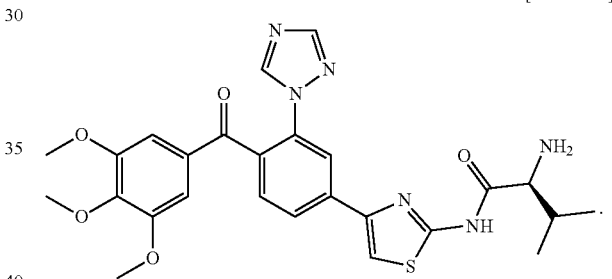

10. The composition according to claim 9, wherein the pharmaceutically acceptable salt of (S)—N-(4-(3-(1H-1,2,4-triazole-1-yl)-4-(3,4,5-trimethoxybenzoyl)phenyl)thiazole-2-yl)-2-amino-3-methylbutanamide is hydrochloride.

11. The method according to claim 7, wherein the immune checkpoint inhibitor is the anti-PD-1 antibody, the anti-CTLA-4 antibody or both thereof.

12. The method according to claim 7, wherein the immune checkpoint inhibitor is the anti-PD-1 antibody and the anti-CTLA-4 antibody.

13. The method according to claim 7, wherein the cancer is one selected from the group consisting of colorectal cancer, skin melanoma, lung cancer, gastric cancer, prostate cancer, lymphoma, merkel cell carcinoma, urinary tract neoplasm and multiple myeloma.

14. The method according to claim 7, wherein (S)—N-(4-(3-(1H-1,2,4-triazole-1-yl)-4-(3,4,5-trimethoxybenzoyl)phenyl)thiazole-2-yl)-2-amino-3-methylbutanamide or the pharmaceutically acceptable salt thereof are orally administered.

15. The method according to claim 7, wherein the immune checkpoint inhibitor is parenterally administered.

* * * * *